US010480306B2

(12) United States Patent
Guo et al.

(10) Patent No.: US 10,480,306 B2
(45) Date of Patent: Nov. 19, 2019

(54) CEMENT EVALUATION WITH NEUTRON-NEUTRON MEASUREMENT

(71) Applicant: Halliburton Energy Services, Inc., Houston, TX (US)

(72) Inventors: Weijun Guo, Houston, TX (US); Daniel F. Dorffer, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/039,366

(22) PCT Filed: Dec. 30, 2013

(86) PCT No.: PCT/US2013/078285
§ 371 (c)(1),
(2) Date: May 25, 2016

(87) PCT Pub. No.: WO2015/102574
PCT Pub. Date: Jul. 9, 2015

(65) Prior Publication Data
US 2017/0167243 A1 Jun. 15, 2017

(51) Int. Cl.
*E21B 47/00* (2012.01)
*G01N 23/05* (2006.01)
(Continued)

(52) U.S. Cl.
CPC ....... *E21B 47/0005* (2013.01); *G01N 23/025* (2013.01); *G01N 23/05* (2013.01);
(Continued)

(58) Field of Classification Search
None
See application file for complete search history.

(56) References Cited

U.S. PATENT DOCUMENTS

| 2,231,577 A | 2/1941 | Hare |
| 3,930,153 A | 12/1975 | Scott |

(Continued)

FOREIGN PATENT DOCUMENTS

| EP | 0443936 A1 | 8/1991 |
| GB | 2037439 A | 7/1980 |

(Continued)

OTHER PUBLICATIONS

"International Application Serial No. PCT/US2013/078285, Response filed Apr. 24, 2015 to Written Opinion dated Sep. 29, 2014", 3 pgs.
(Continued)

*Primary Examiner* — Edwin C Gunberg
(74) *Attorney, Agent, or Firm* — Gilliam IP PLLC (57) ABSTRACT

Various embodiments include apparatus and methods to conduct neutron-neutron measurements and to evaluate quality of cement between a casing and a formation. A tool can include a neutron source, a far detector, and a near detector, where the far detector and the near detector detect neutrons in response to activation of the neutron source. Measured counts of the detected neutrons can be compared with respect to expected counts of neutrons. From one or more comparisons, the quality of the cement can be evaluated. Additional apparatus, systems, and methods are disclosed.

16 Claims, 5 Drawing Sheets

(51) Int. Cl.
*G01N 23/02* (2006.01)
*G01N 33/38* (2006.01)
*E21B 33/14* (2006.01)

(52) U.S. Cl.
CPC ............ *G01N 33/383* (2013.01); *E21B 33/14* (2013.01); *G01N 2223/304* (2013.01); *G01N 2223/646* (2013.01)

(56) References Cited

U.S. PATENT DOCUMENTS

| | | | | |
|---|---|---|---|---|
| 4,004,147 | A | * | 1/1977 | Allen ..................... G01V 5/107 250/262 |
| 4,092,536 | A | * | 5/1978 | Smith ..................... G01V 5/107 250/265 |
| 4,384,205 | A | | 5/1983 | Flaum |
| 4,459,480 | A | * | 7/1984 | Dimon .................... E21B 43/04 166/312 |
| 4,507,554 | A | | 3/1985 | Hertzog et al. |
| 4,698,500 | A | | 10/1987 | Scala |
| 4,810,876 | A | | 3/1989 | Wraight et al. |
| 5,578,820 | A | | 11/1996 | Gadeken et al. |
| 5,783,822 | A | | 7/1998 | Buchanan et al. |
| 2006/0233048 | A1 | * | 10/2006 | Froelich ............. E21B 47/0005 367/35 |
| 2009/0205825 | A1 | * | 8/2009 | Smith, Jr. ............... E21B 43/26 166/280.1 |
| 2012/0031613 | A1 | | 2/2012 | Green |
| 2012/0075953 | A1 | | 3/2012 | Chace et al. |
| 2012/0175511 | A1 | * | 7/2012 | Masnyk .................. E21B 43/26 250/259 |
| 2013/0062057 | A1 | | 3/2013 | Smith, Jr. |
| 2013/0261974 | A1 | | 10/2013 | Stewart et al. |
| 2013/0345983 | A1 | * | 12/2013 | Guo ....................... G01V 5/104 702/8 |
| 2015/0108339 | A1 | | 4/2015 | Guo et al. |

FOREIGN PATENT DOCUMENTS

| | | |
|---|---|---|
| WO | 2011127156 A2 | 10/2011 |
| WO | WO-2012083210 A2 | 6/2012 |
| WO | WO-2015102574 A1 | 7/2015 |

OTHER PUBLICATIONS

Anderson, Warren L., et al., "Acoustic Cement Bond Logging", *SPWLA 2nd Annual Logging Symposium*, May 18-19, Dallas, Texas, (1961), 14 pgs.
"Application Serial No. PCT/US2013/078285, International Preliminary Report on Patentability dated Nov. 23, 2015", 4 pgs.
"International Application Serial No. PCT/US2013/078285, International Search Report dated Sep. 29, 2014", 3 pgs.
"International Application Serial No. PCT/US2013/078285, Written Opinion dated Sep. 29, 2014", 7 pgs.
Anderson, Warren L., et al., "Acoustic Cement Bond Logging", SPWLA 2nd Annual Logging Symposium, May 18-19, Dallas, Texas, (1961).
GCC Application Serial No. GC 2014-28675, GCC Second Examination Report; dated Jan. 21, 2018, 5 Pages.
GCC application serial No. GC 2014-28675, First Examination Report, dated Sep. 28, 2017, 5 pages.
EP application serial No. 13900836, EP Search Report, dated Aug. 3, 2017, 7 pages.
EP Application Serial No. 15908961.4, Extended European Search Report, dated Sep. 27, 2018, 10 pages.
International Application Serial No. PCT/US2015/061572, International Search Report dated Aug. 19, 2016, 3 pages.
International Application Serial No. PCT/US2015/061572, Written Opinion dated Aug. 19, 2016, 10 pages.
U.S. Appl. No. 15/757,613, Final Office Action, dated Feb. 1, 2019, 8 pages.
GCC Application Serial No. 201428675; GCC Examination Report; dated Aug. 15, 2018, 4 Pages.

\* cited by examiner

CEMENT EVALUATION WITH NEUTRON-NEUTRON MEASUREMENT

PRIORITY APPLICATION

This application is a U.S. National Stage Filing under 35 U.S.C. 371 from International Application No. PCT/2013/078285, filed on 30 Dec. 2013, and published as WO 2015/102574 A1 on 9 Jul. 2015, which applications and publication are incorporated herein by reference in their entirety.

TECHNICAL FIELD

The present invention relates generally to apparatus and methods of making and evaluating measurements.

BACKGROUND

Cement is typically provided between a casing and a formation to occupy the annular space between the casing and the formation of a wellbore. The cement has a height that effectively provides a plug to prevent fluid flow, which isolates a lower zone from an upper zone with respect to the plug. Successful primary cementing operations result in a cement sheath to bond and support casing and provide zonal isolation. Inter-zonal flow may occur as fluid migrates due to differential pressure between two zones. A continuous void in the cement may allow migration of fluid, which is undesirable. Good zonal isolation helps prevent the loss of production, control inter-zonal flow and/or flow to the surface, reduce water production, and improve confinement of stimulation treatments. Stimulation treatments are applied to a formation does not easily produce hydrocarbons. An example stimulation treatment includes using acids to increase channels that make paths to enhance flow of hydrocarbons into a wellbore. Another example stimulation treatment includes using hydraulic pressure to create factures to enhance flow of hydrocarbons into a wellbore. The physio-mechanical properties of the cement need to be optimized for the specific attributes of each well. For example, weak formations with low fracture gradients use low-density cement systems to reduce the hydrostatic pressure of the fluid column during cement placement.

A cement evaluation log was introduced around the 1960s with sonic attenuation measurements. Through more than 50 years of evolution, the acoustic solutions now consist of sonic attenuation measurement with borehole compensation and ultrasonic impedance imaging with azimuthal sensitivity. These evaluation technologies are being challenged to meet new environmental conditions (such as deep water) and new regulatory requirements. The acoustic impedance contrasts between heavy drilling mud and light cement for example may be close to or beyond the measurement sensitivity limitations of existing sensors, while heavy casings present an additional technical barrier for the traditional acoustic solutions.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Various embodiments include apparatus and methods to conduct neutron-neutron measurements and to evaluate quality of cement between a casing and a formation. A neutron-neutron measurement is a measurement in which neutrons are generated from a source and neutrons are detected at a detector in response to the generation of neutrons. A tool can include a neutron source, a far detector, and a near detector, where the far detector and the near detector detect neutrons in response to activation of the neutron source. Measured counts of the detected neutrons can be compared with respect to expected counts of neutrons. From one or more comparisons, the quality of the cement can be evaluated.

In various embodiments, techniques can be performed to utilize neutron-neutron measurements for cement evaluation application. Such techniques can provide a corroborative and quantitative measure for cement quality. Neutron-neutron devices have been utilized for rock porosity measurement with downhole tools. The devices typically consist of two neutron detectors and a neutron production source. The neutron production source can include, but is not limited to, an americium/beryllium (Am/Be) source, a californium-252 (Cf-252) source, or a pulsed-neutron generator.

To evaluate cement quality, a cement flurry for the cement in a wellbore can be mixed with materials that are dopants to the cement, where the dopants are of high neutron capture cross section, such as boron or gadolinium. Other dopants may be used that have a neutron capture cross section that is in the range of the neutron capture cross sections of boron or gadolinium. The dopants can be distributed homogeneously in the cement flurry such that the dopants are homogenously distributed in the cement formed in the wellbore. A void at a particular depth has less cement around the casing than at a depth at which there is no void or similar defective and less dopants, since the dopants are homogeneously mixed. When logging using a neutron-neutron tool, the dopants would lead to lower near (n) and far(f) counts by neutron detectors used, and larger near/far count ratios (n/f ratios). When evaluation of a cement log is performed, zones of poor cement demonstrate a trend of lower near and far counts (n/f) and higher n/f ratio when compared to expected n/f and n/f ratio for the cement without voids.

Figure 1:
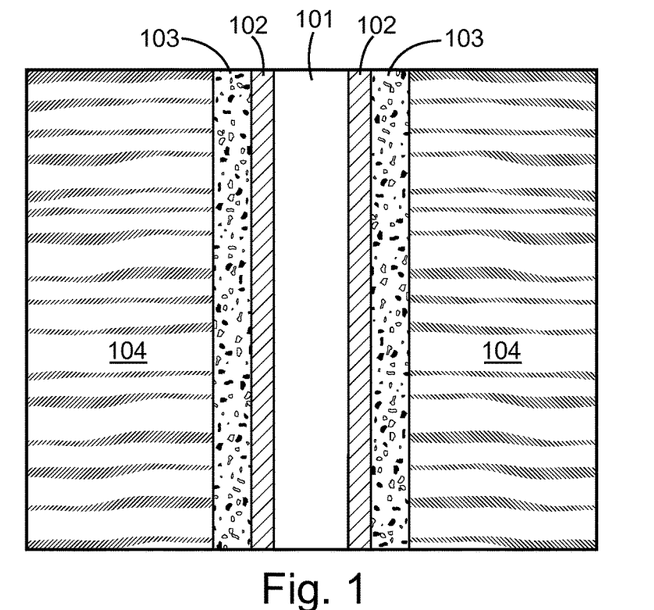
FIG. 1 is a schematic representation of a cased-hole completion geometry.

FIG. 1 is a schematic representation of a cased-hole completion geometry. The cased-hole completion geometry includes a borehole 101, a casing 102, cement 103, and a formation 104. This completion geometry shows a borehole-casing-cement-formation region in which there is no void or other similar defective. Neutron-neutron measurements of this geometry can provide n/f and n/f ratio values that can act as a baseline for measurements of other regions. A log of parameters acquired from the neutron-measurements along the casing can be generated.

Figure 2:
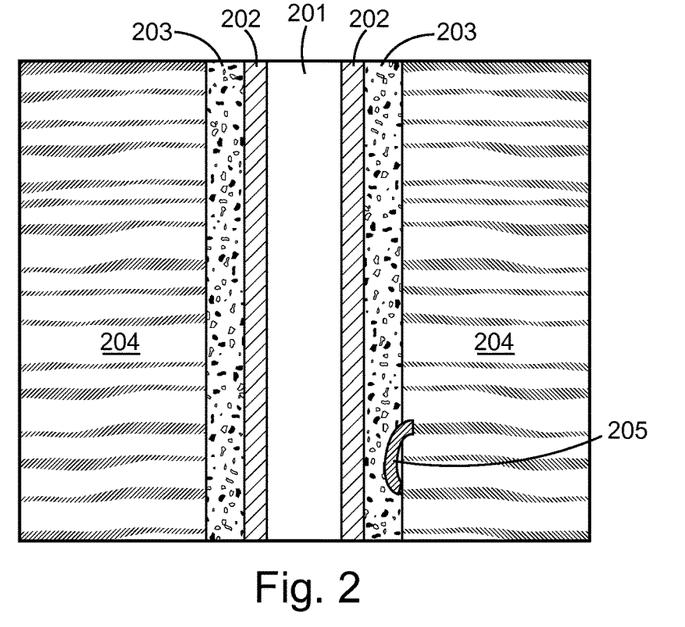
FIG. 2 is a schematic representation of a cased-hole completion geometry in which channeling has occurred.

FIG. 2 is a schematic representation of a cased-hole completion geometry in which channeling has occurred. The cased-hole completion geometry, in this situation, includes a borehole 201, a casing 202, cement 203, a formation 204, and a channeling 205. Channeling can occur as a result of poor cement completion. Channeling 205 is a substantially continuous void path. When cement has voids, neutron counts deviate from expected reading. When channeling occurs for poor cement completion, a pattern of lower n/f counts, higher n/f ratio can be determined from neutron-neutron measurements. With this pattern compared to an expected pattern, this region containing the channeling 205 can be flagged as being a region of poor cement completion. The expected pattern may be a baseline stored in a memory, a separate log generated while the isolation was good at the measured region, a pattern of another region along the casing 202 determined to be of good quality cement, an expected pattern generated from modeling or simulation, or other representation of good quality cement deployment.

Figure 3:
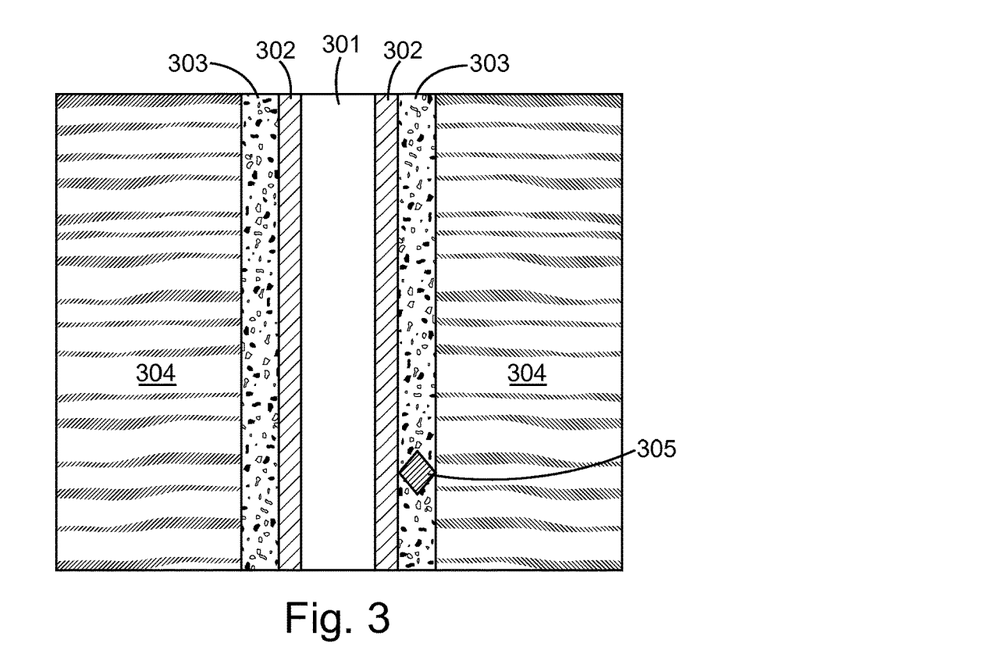
FIG. 3 is a schematic representation of a cased-hole completion geometry having gas-contaminated cement.

FIG. 3 is a schematic representation of a cased-hole completion geometry having gas-contaminated cement. The cased-hole completion geometry, in this situation, includes a borehole 301, a casing 302, cement 303, a formation 304, and a gas-contaminated section 305. For gas-contaminated cement, a pattern of lower n/f counts and higher n/f ratio can be acquired in a statistical manner. The statistical manner occurs for the gas-contaminated region due this region not being a connected series of voids as in a channeling, such that spikes appear in the tread of the measurements, which is a statistical fluctuation between measurements associated with a baseline of expected results of good quality cement and measurements associated with a channeling.

Poor quality cement may be defined as a selected value below an expected n/f, a selected value above an expected n/f ratio, or both a selected value below an expected n/f and a selected value above an expected n/f ratio. The selected values can be set within a range of the respective expected values. In addition, the selected values can be set to zero such that the respective expected values are selected threshold values for determination of poor quality cement deployment. If the n/f and/or the n/f ratio from measurements compared to expected n/f and n/f ratio indicate poor cement quality, a flag can be set in a measurement system. The generation of the flag may initiate a computation with respect to the void or channel. The computation can use a number of known parameters including the casing size, the borehole size or the caliper (hole size behind the casing), expected amount of cement, and the expected neutron count. The value of the known parameters can be compared with measurements of n/r and/or n/f ratio. From the comparison, the amount of cement missing can be computed or the size of the void or channeling can be computed along the wellbore. With the flag generated and the void/channel computation performed, action can be taken by an operator. In response to a determination that the quality of cement in region is poor, the casing may be perforated to remedially inject cement to fill the void. A measurement process to determine cement quality can include making neutron-neutron measurements along the wellbore/casing of interest and generating a log.

The neutron-neutron measurements can be made using wireline techniques, case line techniques, real time techniques on an electric line, slick line techniques using a memory, or pipe conveyed techniques. In addition, the measurements and analysis are not affected by microannuli filled with gas fill. Microannuli are small gaps between casing and cement that are less than about 40 microns, and, due to their small size, do not impact measurements and are not considered issues with respect to zonal isolation.

The measurement/evaluation procedure may be conducted in which no radioactive material is handled, no radioactive material is present during preparation of the cement mixture, no radioactive material is present during the cementing operation, and no radioactive material is present at any time during the life of the well from this process. Consequently, this procedure provides a safe measurement solution from an environmental perspective.

In various embodiments, a technique can be provided utilizing neutron activation measurement for cement evaluation applications to provide a corroborative and quantitative measure for cement quality. Compared to acoustic solutions, evaluation provided by analysis of neutron-neutron measurements in a manner similar to or identical the techniques taught herein, can provide evaluation that is much less sensitive to drilling mud weight. Deeper depth of investigation provided by the neutron-neutron measurements offers an opportunity to evaluate cement quality between the cement and formation interface.

Figure 4:
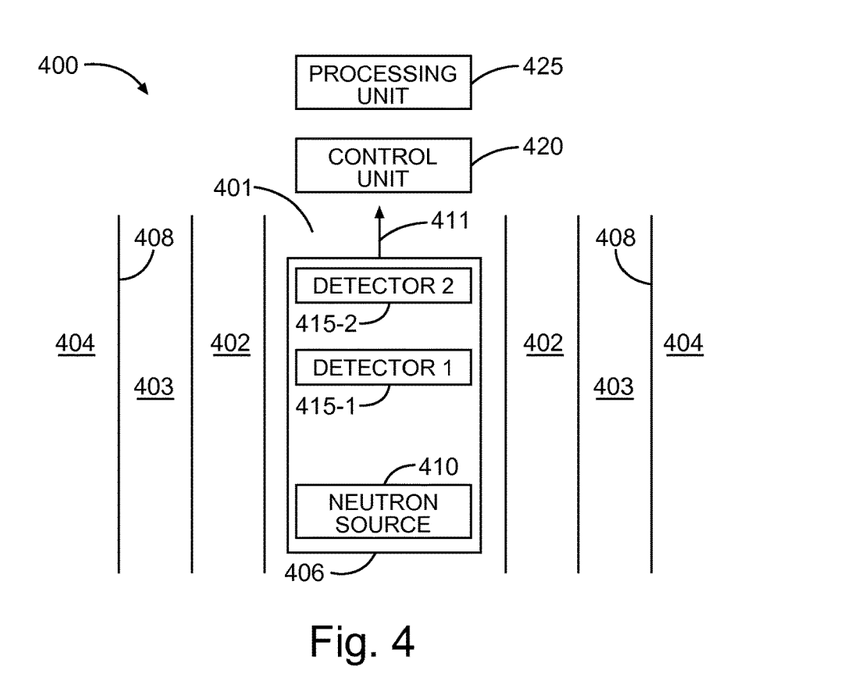
FIG. 4 is a schematic representation of an example system to evaluate cement quality using a neutron-neutron measurement.

FIG. 4 is a schematic representation of an example system 400 to evaluate cement quality using a neutron-neutron measurement. System 400 can include a tool 406 deployable in a cased hole to make measurements. The cased hole includes a casing 402 and cement 403, the cement 403 being between the casing 402 and a wall 408 of a formation 404. The tool 406 can be disposed in casing 402 using a structure 411, providing a wireline application, a case line application, a real time application on an electric line, a slick line application using a memory, or a pipe conveyed application. The cement may be doped with boron or gadolinium. The cement may be doped with an element having a capture cross section approximately equal to or greater than a capture cross section of gadolinium.

The tool 406 can include a neutron source 410, a first detector 415-1, and a second detector 415-2. The first detector 415-1 can be spaced apart from the neutron source 410, where the first detector 415-1 has a capability to detect neutrons. The second detector 415-2 can be spaced apart from the neutron source 410, where the second detector 415-2 has a capability to detect neutrons. The first detector 415-1 and the second detector 415-2 can be arranged with respect to each other and neutron source 410, such that the second detector 415-2 can provide a far count of detected neutrons relative to the first detector operable to provide a near count of detected neutrons.

The tool 406 may include a number neutron sources and a number of detectors greater than two. The neutron source 410 and other neutron sources of the tool 406 may be realized in a number of different formats. The different formats may include one or more pulsed-neutron sources, one or more radionuclide sources, or other types of neutron generators. The radionuclide sources can include, but are not limited to, Am/Be sources or Cf-252 sources. An AmBe source can be made by mixing americium-241 with beryllium. The detectors 415-1 and 415-2 and other detectors may be realized in a number of different formats. The different formats of detectors 415-1 and 415-2 may include, but are not limited to, sodium-iodide detectors. The system 400 can include instrumentality in conjunction with detectors 415-1 and 415-2 and other detectors to make near and far counts and to generate near/far count ratios of neutrons detected from regions exterior to the tool 206 in response to neutrons generated from the neutron source 410 or other neutron sources of the tool 406. The instrumentality may be realized by a processing unit 425 of system 400 or components of detectors 415-1 and 415-2.

The processing unit 425 can be arranged to operatively evaluate cement quality using a neutron-neutron measurement. The processing unit 425 can operatively evaluate a quality of the cement from a comparison of a measured pattern to an expected pattern. The measured pattern can be generated from use of the neutron source 210, the first detector 415-1, and the second detector 415-2, and the measured pattern may include measured near and far counts, a measured near count to far count ratio, or both measured near and far counts and measured near count to far count ratio. The expected pattern, to correspond to the features of the measured pattern, can include expected near and far counts, an expected near count to far count ratio, or both expected near and far counts and an expected near count to far count ratio. The expected pattern at a measured region can be a baseline pattern stored in a memory, can be from a separate log generated while isolation was good at the measured region, or can be a pattern of another region along the casing determined to be of good quality cement. The processing unit 425 can include circuitry to set a flag indicative of poor quality cement if the measured near and far counts are less than the expected near and far counts by a first selected amount or if the measured near count to far count ratio is greater than the expected near count to far count ratio by a second selected amount. The circuitry can include a memory and a processor. The processing unit 425 can operatively determine whether a void or a channeling is present in the cement. The processing unit 425 can have computation capabilities to determine a size of a void or a channeling in the cement.

The system can include a control unit 420 to manage operation of the neutron source 410 and the detectors 415-1 and 415-2. The control unit 420 and the processing unit 425 may be integrated with each other. The control unit 420 and the processing unit 425 may be integrated with the tool 406 operable downhole. The control unit 425 and the processing unit 425 may have distributed components. Distributed components may include components downhole in the vicinity of the tool 406 deployed for operation and components at the surface or at locations between the surface and the vicinity of the operational tool 406.

Figure 5:
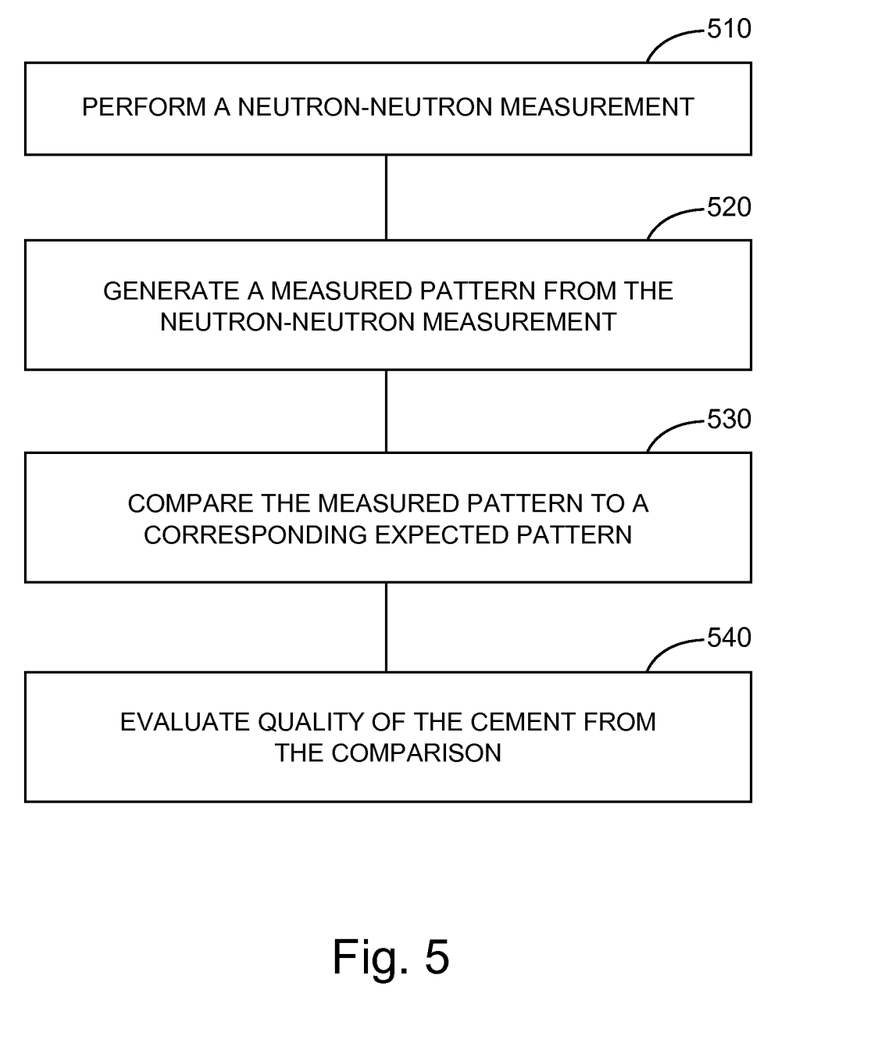
FIG. 5 is a flow diagram of features of an example method of evaluating quality of cement around a casing.

FIG. 5 is a flow diagram of features of an example method of evaluating quality of cement around a casing. At 510, a neutron-neutron measurement is performed. The neutron-neutron measurement is performed in a borehole, where the borehole is surrounded by a casing, cement, and a formation. Performing the neutron-neutron measurement can include performing a neutron-neutron measurement in which the cement is doped with boron or gadolinium. Performing the neutron-neutron measurement can include performing a neutron-neutron measurement in which the cement is doped with an element having a capture cross section approximately equal to or greater than a capture cross section of gadolinium.

At 520, a measured pattern is generated from the neutron-neutron measurement. The measured pattern can include measured near and far counts of neutrons, a measured near count to far count ratio of neutrons, or both measured near and far counts of neutrons and measured near count to far count ratio of neutrons. At 530, the measured pattern is compared to a corresponding expected pattern. The expected pattern can include expected near and far counts of neutrons, an expected near count to far count ratio of neutrons, or both expected near and far counts of neutrons and an expected near count to far count ratio of neutrons. The expected pattern at a measured region can be a baseline pattern stored in a memory, can be from a separate log generated while isolation was good at the measured region, or can be a pattern of another region along the casing determined to be of good quality cement.

At 540, quality of the cement from the comparison is evaluated. Evaluating the quality of the cement can include generating a flag indicating poor quality if the measured near and far counts are less than the expected near and far counts by a first selected amount or if the measured near count to far count ratio is greater than the expected near count to far count ratio by a second selected amount. Evaluating the quality of the cement can include determining whether a void or a channeling is present in the cement. In various embodiments, a size of a void or a channeling in the cement can be computed.

In various embodiments, components of a system operable to conduct neutron-neutron measurements and analyze the measurements, as described herein or in a similar manner, can be realized in combinations of hardware and processor-based devices, or in simulations. These implementations can include a machine-readable storage device having machine-executable instructions, such as a computer-readable storage device having computer-executable instructions, which instructions when executed cause a machine to perform operations. The execution can be conducted under the control of one or more processors. The operations can include operations to generate a measured pattern from performing a neutron-neutron measurement in a borehole, the borehole surrounded by a casing, cement, and a formation, the measured pattern including measured near and far counts, a measured near count to far count ratio, or both measured near and far counts and measured near count to far count ratio; to compare the measured pattern to a corresponding expected pattern, the expected pattern including expected near and far counts, an expected near count to far count ratio, or both expected near and far counts and an expected near count to far count ratio; and to evaluate quality of the cement from the comparison. The instructions can include instructions to provide data to a processing unit such that the processing unit can conduct one or more processes to evaluate signals, data, or signals and data. In various embodiments, a machine-readable storage device or devices having instructions stored thereon, which, when performed by a machine, can cause the machine to perform operations, the operations including performing any one of the processes or similar processes as taught herein. Further, a machine-readable storage device, herein, is a physical device that stores data represented by physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Figure 6:
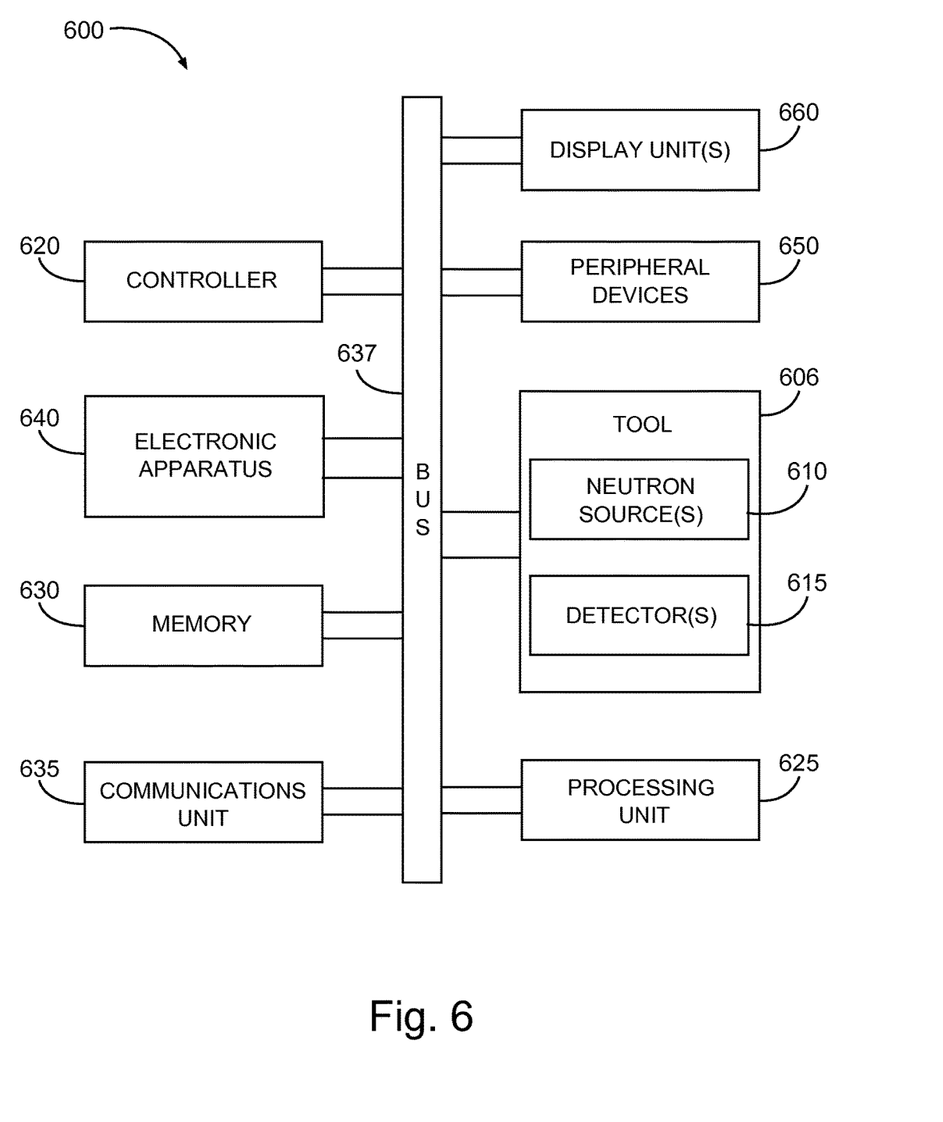
FIG. 6 is a block diagram of an example system operable to determine quality of cement using neutron-neutron measurement

FIG. 6 is a block diagram of an example system 600 operable to determine quality of cement using neutron-neutron measurement, as described herein or in a similar manner. The system 600 can include a tool 606 having an arrangement of neutron source(s) 610 and detector(s) 615 that can be realized in a similar or identical manner to arrangements and processing discussed herein. One of the detector(s) 615 can be arranged as a near detector and another one of the detector(s) can be arranged as a far detector, where near and far is relative to the locations of these two detectors with respect to each other and at least one of the neutrons sources 610(*s*). The system 600 can be configured to operate in accordance with the teachings herein to perform neutron-neutron measurements and to determine quality of cement between a casing and a formation.

The system 600 can include a controller 620, a memory 630, an electronic apparatus 640, and a communications unit 635. The memory 630 can be structured to include a database. The controller 620, the memory 630, and the communications unit 635 can be arranged to operate as a processing unit to control operation of the neutron source(s) 610 and the detector(s) 615 and to perform operations on the signals collected by the detector(s) 615 to conduct evaluation of cement between a casing and a formation. A processing unit 625, structured to conduct such evaluation using neutron-neutron measurements, can be implemented as a single unit or distributed among the components of the system 600 including electronic apparatus 640. The electronic apparatus 640 can provide other circuitry for operation of the system 600. The controller 620 and the memory 630 can operate to control activation of the neutron source(s) 610 to generate neutron pulses. The controller 620 and the memory 630 can operate to control selection of the detector(s) 615 in the tool 606 and to manage processing schemes. The controller 620, the memory 630, and other components of the system 600 can be configured, for example, to operate similar to or identical to the components discussed herein or similar to or identical to any of methods discussed herein.

The communications unit 635 can include downhole communications for appropriately located sensors in a wellbore. Such downhole communications can include a telemetry system. The communications unit 635 may use combinations of wired communication technologies and wireless technologies at frequencies that do not interfere with on-going measurements.

The system 600 can also include a bus 637, where the bus 637 provides electrical conductivity among the components of the system 600. The bus 637 can include an address bus, a data bus, and a control bus, each independently configured or in an integrated format. The bus 637 can be realized using a number of different communication mediums that allows for the distribution of components of the system 600. The bus 637 can include a network. Use of the bus 637 can be regulated by the controller 620.

In various embodiments, the peripheral devices 650 can include additional storage memory and other control devices that may operate in conjunction with the controller 620 and the memory 630. In an embodiment, the controller 620 can be realized as a processor or a group of processors that may operate independently depending on an assigned function.

The system 600 can include display unit(s) 660 as a distributed component on the surface of a wellbore, which can be used with instructions stored in the memory 630 to implement a user interface to monitor the operation of the tool 606 or components distributed within the system 600. The user interface may be used to input parameter values for thresholds such that the system 600 can operate autonomously substantially without user intervention in a variety of applications. The user interface can also provide for manual override and change of control of the system 600 to a user. Such a user interface can be operated in conjunction with the communications unit 635 and the bus 637.

Figure 7:
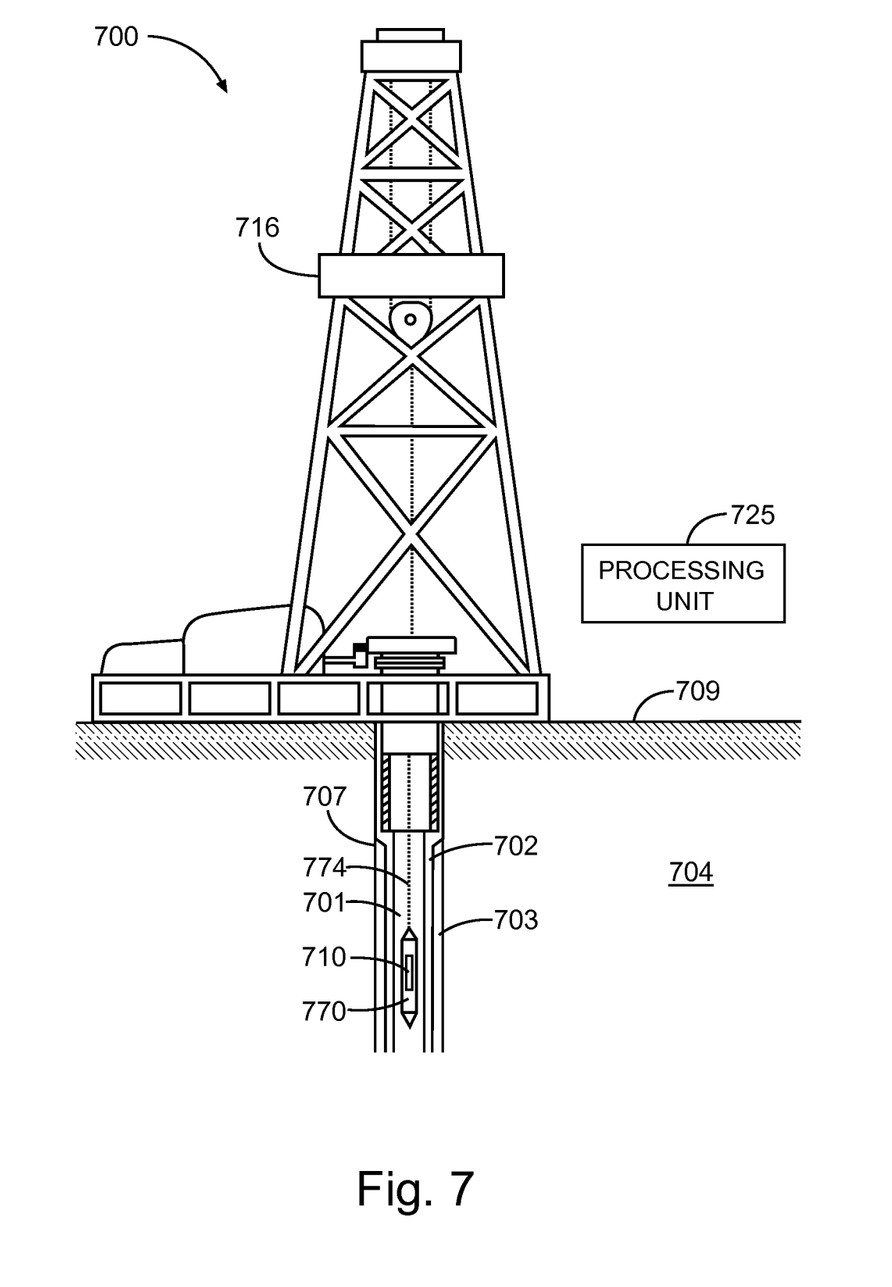
FIG. 7 is a block diagram of an example system at a well site, where the system is operable to evaluate quality of cement using neutron-neutron measurement.

FIG. 7 is a block diagram of an example system 700 at a well site, where the system 700 is operable to evaluate quality of cement using neutron-neutron measurement. The system 700 can include a tool 706 to conduct measurements using a neutron source, a near detector, and a far detector and to conduct analysis of the measurements as taught herein. Tool 706 can be realized in a similar or identical manner to arrangements taught herein to generate neutrons and to detect neutrons.

System 700 can include a rig 716 located at a surface 709 of a well 707. In various embodiments, tool 706 may be included in a tool body 770 coupled to a structure 774, providing a wireline application, a case line application, a real time application on an electric line, a slick line application using a memory, or a pipe conveyed application. The tool body 770 can be lowered into a borehole 701 surrounded by a casing 702, cement 703, where the cement 703 separates the casing 702 from a formation 704. The tool body 770 containing the tool 706 can include electronics to activate generation of neutron pulses from neutron source(s) of tool 706 towards formation 704 separated from tool body 770 by portions of the borehole 701, the casing 702, and the cement 703 being analyzed and to collect responses from detector(s) of tool 706. Such electronics can include a processing unit to provide analysis of neutron-neutron measurements, including an evaluation of quality of the cement 703 to the surface 709 over a standard communication mechanism for operating in a well. Alternatively, electronics can include a communications interface to provide signals output by detector(s) of tool 706 to the surface 709 over a standard communication mechanism for operating in a well, where these output signals can be analyzed at a processing unit 725 at the surface to determine quality of the cement 703. The structure 774 may be realized as a wireline (multiple power and communication lines), a mono-cable (a single conductor), and/or a slick-line (no conductors for power or communications), or other appropriate structure for use in the borehole 701.

In various embodiments, a method can include processes to perform neutron-neutron measurements and analyze the measurements to evaluate cement quality, where the method has various combinations of features as described herein. In various embodiments, a method 1 comprises: performing a neutron-neutron measurement in a borehole, the borehole surrounded by a casing, cement, and a formation; generating a measured pattern from the neutron-neutron measurement, the measured pattern including measured near and far counts of neutrons, a measured near count to far count ratio of neutrons, or both measured near and far counts of neutrons and measured near count to far count ratio of neutrons; comparing the measured pattern to a corresponding expected pattern, the expected pattern including expected near and far counts of neutrons, an expected near count to far count ratio of neutrons, or both expected near and far counts of neutrons and an expected near count to far count ratio of neutrons; and evaluating quality of the cement from the comparison.

A method 2 can include the features of method 1 and can include evaluating the quality of the cement to include generating a flag indicating poor quality if the measured near and far counts are less than the expected near and far counts by a first selected amount or if the measured near count to far count ratio is greater than the expected near count to far count ratio by a second selected amount.

A method 3 can include the features of any of methods 1 and 2 and can include evaluating the quality of the cement to include determining whether a void or a channeling is present in the cement.

A method 4 can include the features of any of methods 1-3 and can include computing a size of a void or a channeling in the cement.

A method 5 can include the features of any of methods 1-4 and can include performing the neutron-neutron measurement to include performing a neutron-neutron measurement in which the cement is doped with boron or gadolinium.

A method 6 can include the features of any of methods 1-4 and can include performing the neutron-neutron measurement to include performing a neutron-neutron measurement in which the cement is doped with an element having a capture cross section approximately equal to or greater than a capture cross section of gadolinium.

A method 7 can include the features of any of methods 1-6 and can include the expected pattern at a measured region to be a baseline pattern stored in a memory, to be from a separate log generated while isolation was good at the measured region, or to be a pattern of another region along the casing determined to be of good quality cement. Features of any of methods 1-7 or other combinations of features, as taught herein, may be combined into a procedure according to the teachings herein.

In various embodiments, a machine-readable storage device 1 has instructions stored thereon, which, when performed by a machine, cause the machine to perform operations, the operations comprising operations to: generate a measured pattern from performing a neutron-neutron measurement in a borehole, the borehole surrounded by a casing, cement, and a formation, the measured pattern including measured near and far counts, a measured near count to far count ratio, or both measured near and far counts and measured near count to far count ratio; compare the measured pattern to a corresponding expected pattern, the expected pattern including expected near and far counts, an expected near count to far count ratio, or both expected near and far counts and an expected near count to far count ratio; and evaluate quality of the cement from the comparison.

A machine-readable storage device 2 can include the features of machine-readable storage device 1 and can include operations to evaluate the quality of the cement to include generation of a flag indicating poor quality if the measured near and far counts are less than the expected near and far counts by a first selected amount or if the measured near count to far count ratio is greater than the expected near count to far count ratio by a second selected amount.

A machine-readable storage device 3 can include the features of machine-readable storage devices 1 and 2 and can include operations to evaluate the quality of the cement to include determination of whether a void or a channeling is present in the cement.

A machine-readable storage device 4 can include the features of any of machine-readable storage devices 1-3 and can include operations to include operations to compute a size of a void or a channeling in the cement.

A machine-readable storage device 5 can include the features of any of machine-readable storage devices 1-4 and can include the cement being doped with boron or gadolinium.

A machine-readable storage device 6 can include the features of any of machine-readable storage devices 1-4 and can include the cement being doped with an element having a capture cross section approximately equal to or greater than a capture cross section of gadolinium.

A machine-readable storage device 7 can include the features of any of machine-readable storage devices 1-6 and can include the expected pattern at a measured region being a baseline pattern stored in a memory, being from a separate log generated while isolation was good at the measured region, or being a pattern of another region along the casing determined to be of good quality cement.

A machine-readable storage device 8 can have instructions stored thereon, which, when performed by a machine, cause the machine to perform operations, the operations comprising operations to perform any of the methods 1-7 or other combinations of features as taught herein.

In various embodiments, an system 1 comprises: a neutron source operable to probe a region in a borehole, the region of the borehole surrounded by a casing, cement, and a formation; a first detector spaced apart from the neutron source, the detector having a capability to detect neutrons; a second detector spaced apart from the neutron source, the second detector having a capability to detect neutrons including providing a far count of detected neutrons relative to the first detector providing a near count of detected neutrons; and a processing unit to operatively evaluate quality of the cement from a comparison of a measured pattern to an expected pattern, the measured pattern generated from use of the neutron source, the first detector, and the second detector, the measured pattern including measured near and far counts, a measured near count to far count ratio, or both measured near and far counts and measured near count to far count ratio, the expected pattern including expected near and far counts, an expected near count to far count ratio, or both expected near and far counts and an expected near count to far count ratio.

A system 2 can include the features of system 1 and can include the processing unit to include circuitry to set a flag indicative of poor quality if the measured near and far counts are less than the expected near and far counts by a first selected amount or if the measured near count to far count ratio is greater than the expected near count to far count ratio by a second selected amount.

A system 3 can include the features of any of systems 1 and 2 and can include the processing unit to operatively evaluate the quality of the cement to include the processing unit to operatively determine whether a void or a channeling is present in the cement.

A system 4 can include the features of any of systems 1-3 and can include the processing unit to include computation capabilities to determine a size of a void or a channeling in the cement.

A system 5 can include the features of any of systems 1-4 and can include the cement is doped with boron or gadolinium.

A system 6 can include the features of any of systems 1-4 and can include the cement is doped with an element having a capture cross section approximately equal to or greater than a capture cross section of gadolinium.

A system 7 can include the features of any of systems 1-6 and can include the expected pattern at a measured region being a baseline pattern stored in a memory, being from a separate log generated while isolation was good at the measured region, or being a pattern of another region along the casing determined to be of good quality cement.

A system 8 can include a neutron source operable to probe a region in a borehole, the region of the borehole surrounded by a casing, cement, and a formation; a first detector spaced apart from the neutron source, the detector having a capability to detect neutrons; a second detector spaced apart from the neutron source, the second detector having a capability to detect neutrons including providing a far count of detected neutrons relative to the first detector providing a near count of detected neutrons; and a processing unit having a machine-readable storage device, wherein the neutron source, the first detector, the second detector, and the processing unit are structured to perform any of the methods of claims 1-7 or other operational features taught herein. Features of any of system 1-8 or other combinations of features, as taught herein, may be combined into a system according to the teachings herein.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
   mixing neutron absorbing dopant material with cement flurry for an annular cement structure in a borehole;
   performing a neutron-neutron measurement in the borehole, the borehole surrounded by a casing, the annular cement structure, and a formation;
   generating a measured pattern from the neutron-neutron measurement, the measured pattern including measured near and far counts of neutrons and measured near count to far count ratio of neutrons;
   comparing the measured pattern to a corresponding expected pattern, the corresponding expected pattern including expected near and far counts of neutrons representing cement without voids and an expected near count to far count ratio of neutrons representing cement without voids; and
   evaluating quality of the cement from the comparison.

2. The method of claim 1, wherein evaluating the quality of the cement includes generating a flag indicating poor quality if the measured near and far counts are less than the expected near and far counts by a first selected amount and if the measured near count to far count ratio is greater than the expected near count to far count ratio by a second selected amount.

3. The method of claim 1, wherein evaluating the quality of the cement includes determining whether a defect is present in the cement based on the measured near and far counts being less than the expected near and far counts, and the measured near count to far count ratio being greater than the expected near count to far count ratio.

4. The method of claim 1, wherein the method includes computing a size of a void or a channeling in the cement.

5. The method of claim 1, wherein performing the neutron-neutron measurement includes performing a neutron-neutron measurement in which the cement is doped with boron or gadolinium.

6. The method of claim 1, wherein performing the neutron-neutron measurement includes performing a neutron-neutron measurement in which the cement is doped with gadolinium.

7. The method of claim 1, wherein evaluating the quality of the cement comprises detecting at least one of a void and a channeling in the cement in response tolll the near and far counts of neutrons being less than the expected near and far counts of neutrons, and the near count to far count ratio of neutrons being larger than the expected near count to far count ratio of neutrons.

8. A system comprising:
   a neutron source positioned in a region in a borehole, the region of the borehole surrounded by a casing, a cement formed from a cement flurry mixed with a neutron absorbing material, and a formation;
   a first neutron detector spaced apart from the neutron source and configured to provide a near count of detected neutrons;
   a second neutron detector spaced apart from the neutron source, the second neutron detector configured to provide a far count of detected neutrons relative to the first neutron detector; and
   a processing unit configured to evaluate quality of the cement by comparing a measured pattern to an expected pattern, the measured pattern including a measured near count from the first neutron detector, a measured far count from the second neutron detector, and a measured near count to far count ratio, the expected pattern including expected near and far counts representing cement without voids and an expected near count to far count ratio representing cement without voids.

9. The system of claim 8, wherein the processing unit includes circuitry to set a flag indicative of poor quality if the measured near and far counts are less than the expected near and far counts by a first selected amount and if the measured near count to far count ratio is greater than the expected near count to far count ratio by a second selected amount.

10. The system of claim 8, wherein the processing unit to operatively evaluate the quality of the cement includes the processing unit configured to operatively determine whether a void or a channeling is present in the cement.

11. The system of claim 8, wherein the processing unit includes computation capabilities to determine a size of a void or a channeling in the cement.

12. The system of claim 8, wherein the cement is doped with boron or gadolinium.

13. The system of claim 8, wherein the cement is doped with gadolinium.

14. The system of claim 8, wherein the processing unit is configured to operatively detect at least one of a void and a channeling in the cement in response to the near and far counts of neutrons being less than the expected near and far counts of neutrons and the near count to far count ratio of neutrons being less than the expected near count to far count ratio of neutrons.

15. A method comprising:
   performing a neutron-neutron measurement in a borehole, the borehole surrounded by a casing, cement, and a formation, wherein the cement includes a mixture of cement flurry and a dopant having a high neutron capture cross-section;
   generating a measured pattern from the neutron-neutron measurement, the measured pattern including a measured near count of neutrons, a measured far count of neutrons, and a near count to far count ratio;
   comparing the measured pattern to a corresponding expected pattern of an expected near count of neutrons representing cement without voids, an expected far count of neutrons representing cement without voids, and an expected near count to far count ratio representing cement without voids; and evaluating quality of the cement from the comparison, wherein evaluating comprises detecting a defect in the cement based on the measured near and far counts being less than the expected near and far counts, and the measured near count to far count ratio being greater than the expected near count to far count ratio.

16. The method of claim 15, wherein evaluating quality of the cement from the comparison comprises determining a size of at least one of a void and a channel based on comparison.

* * * * *

UNITED STATES PATENT AND TRADEMARK OFFICE
CERTIFICATE OF CORRECTION

PATENT NO. : 10,480,306 B2
APPLICATION NO. : 15/039366
DATED : November 19, 2019
INVENTOR(S) : Weijun Guo and Daniel F. Dorffer Page 1 of 1

It is certified that error appears in the above-identified patent and that said Letters Patent is hereby corrected as shown below:

In the Claims

Column 12, Line 1, the portion reading "to]]]" should read --to--.

Signed and Sealed this
Twenty-first Day of July, 2020

Andrei Iancu
*Director of the United States Patent and Trademark Office*